United States Patent
Marino et al.

(10) Patent No.: US 7,162,850 B2
(45) Date of Patent: *Jan. 16, 2007

(54) METHOD OF PACKAGING A BONE ALLOGRAFT INTENDED FOR A SPINAL FUSION PROCEDURE

(75) Inventors: James F. Marino, La Jolla, CA (US); Bryan Cornwall, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/854,663

(22) Filed: May 25, 2004

(65) Prior Publication Data

US 2004/0219505 A1 Nov. 4, 2004

Related U.S. Application Data (62) Division of application No. 09/687,611, filed on Oct. 11, 2000, now Pat. No. 6,739,112.

(60) Provisional application No. 60/226,660, filed on Aug. 21, 2000.

(51) Int. Cl.
 *B65B 55/22* (2006.01)
 *A61F 2/44* (2006.01)

(52) U.S. Cl. .................. 53/431; 53/440; 53/480; 53/485; 128/898; 206/438; 623/23.63

(58) Field of Classification Search .................. 53/428, 53/431–434, 440, 441, 480, 485; 128/898; 206/438; 623/23.63
See application file for complete search history.

(56) References Cited

U.S. PATENT DOCUMENTS

| | | | |
|---|---|---|---|
| 4,065,816 A | | 1/1978 | Sawyer |
| 4,108,161 A | * | 8/1978 | Samuels et al. .............. 600/36 |
| 4,802,853 A | * | 2/1989 | Krasner ...................... 433/215 |
| 5,345,746 A | * | 9/1994 | Franchi ........................ 53/431 |
| 5,385,229 A | * | 1/1995 | Bittmann et al. ........... 206/210 |
| 5,480,424 A | | 1/1996 | Cox |
| 5,531,791 A | | 7/1996 | Wolfinbarger |
| 5,697,383 A | * | 12/1997 | Manders et al. ............. 128/898 |
| 5,820,581 A | * | 10/1998 | Wolfinbarger, Jr. ......... 604/500 |
| 5,977,432 A | * | 11/1999 | Wolfinbarger et al. ...... 128/898 |
| 5,989,498 A | | 11/1999 | Odland |
| 6,024,735 A | * | 2/2000 | Wolfinbarger, Jr. ......... 604/500 |
| 6,189,537 B1 | * | 2/2001 | Wolfinbarger, Jr. ......... 128/898 |
| 6,203,755 B1 | * | 3/2001 | Odland ........................ 422/22 |
| 6,254,635 B1 | * | 7/2001 | Schroeder et al. ......... 623/2.13 |
| 6,293,970 B1 | * | 9/2001 | Wolfinbarger et al. ... 623/23.61 |
| 6,294,187 B1 | | 9/2001 | Boyce et al. |

(Continued)

OTHER PUBLICATIONS

Hsu et al., Bone Grafts and Implants from Spine Care, vol. 2. Mosby 1995. http://www.spine-dr.com/site/surgery/s_bone_grafts.html.*

*Primary Examiner*—Stephen F. Gerrity
(74) *Attorney, Agent, or Firm*—Johnathan D. Spangler (57) ABSTRACT

A system and method of packaging a bone allograft for use in a future medical procedure in which the bone allograft is stored in a saturated saline solution in an airtight container. The saline solution keeps the allograft hydrated and may be saturated with a combination of calcium, phosphate, or magnesium to inhibit mineral leaching out of the allograft during storage. The container may be deformable to conform to the shape of the allograft material as the container is "shrink-fitted" to the allograft. Optionally, the bone allograft may also be freeze-dried prior to placement in the container.

26 Claims, 5 Drawing Sheets

U.S. PATENT DOCUMENTS 6,311,690 B1 * 11/2001 Jefferies ..................... 128/898
6,652,818 B1 * 11/2003 Mills et al. ................. 422/295

2002/0018796 A1 * 2/2002 Wironen ..................... 424/423

* cited by examiner

METHOD OF PACKAGING A BONE ALLOGRAFT INTENDED FOR A SPINAL FUSION PROCEDURE

CROSS-REFERENCES TO RELATED APPLICATIONS

The present application is a divisional of commonly owned U.S. patent application Ser. No. 09/687,611 filed Oct. 11, 2000, now issued as U.S. Pat. No. 6,739,112, the complete disclosure of which is hereby incorporated herein by reference in its entirety for all purposes. Additionally, the present application claims benefit under 35 U.S.C. § 119(e) from U.S. Provisional Application Ser. No. 60/226,660, filed on Aug. 21, 2000, the entire contents of which are hereby expressly incorporated by reference into this disclosure as if set forth fully herein.

TECHNICAL FIELD

The present invention relates to allograft packaging systems, and more particularly to bone allograft packaging systems.

BACKGROUND OF THE INVENTION

Bone allografts are used in a variety of medical procedures, e.g., spinal fusion procedures. Such bone allografts need first to be processed at a sanctioned facility and then are provided to medical facilities that perform the procedures. These processing facilities may shape bone allografts and then package them for transportation to medical facilities. Commonly, the bone allografts are either: (1) fresh frozen or (2) freeze-dried prior to packaging and transportation to a medical facility. Disadvantages exist with both of these approaches. Specifically, fresh frozen bone allografts must be continuously stored at low temperatures (ie: frozen) both when stored and when transported to the medical facility to ensure their suitability for future medical procedures. Disadvantages of requiring such refrigerated storage include both the cost incurred in operating such equipment and the preparation time required in thawing the allografts for use at the start of the medical procedure. Additionally, freeze-dried bone allografts must be re-hydrated prior to use in a medical procedure (which may require some time). Moreover, during the re-hydration process, the bone allograft must be kept in a sterile environment. Due to the time required either to thaw fresh frozen bone allografts or to re-hydrate freeze dried bone allografts, the thawing/re-hydration of the allografts must be commenced at a period of time prior to actually starting the medical procedure, thus increasing the overall time required to perform the surgical procedure.

A further disadvantage of using a freeze-dried bone allograft is that the freeze-drying process reportedly reduces the mechanical properties of the bone (e.g., compressive strength and rigidity). Re-hydrating the bone has been reported to restore only about 90% of the original properties, and this restoration is dependent on physician compliance with the re-hydration process.

Moreover, in certain medical procedures the required size or shape of the bone allograft may not be known a priori. Consequently, it may be necessary to thaw and/or re-hydrate several bone allografts of different sizes and shapes prior to the medical procedure. Those allografts not used during the procedure would then need to be discarded. This is an inefficient use of a limited resource (bone allograft) and is time consuming. Accordingly, a need exists for an improved system for packaging bone allografts for future medical procedures, and in particular a system in which the allografts can be readied for surgical use much more quickly than existing methods allow.

SUMMARY OF THE INVENTION

The present invention includes systems for packaging and storing bone allograft material for future use in medical procedures. In accordance with the present invention, the bone allograft may be placed in a container. In various aspects of the invention, this container may comprise glass, plastic, or a metal foil. A saline solution may be added to the container. In one aspect of the invention, the amount of saline solution added is preferably just sufficient to keep the bone allograft hydrated. In one preferred aspect of the invention, the saline solution is saturated with minerals to minimize the leaching of minerals from the bone over time. The saturation of the saline solution may be accomplished with any combination of minerals, including but not limited to calcium, phosphate and magnesium.

After placing the bone allograft in a saline solution in a container, the container may then optionally be closed with an airtight seal. Prior to the medical procedure, the bone allograft is then simply removed from the container for use. In one optional aspect of the invention, the bone allograft may be sealed in a container first, and solution could subsequently be added to the container via a self-sealing valve. In one approach, air may be vacuumed from the container prior to closing the container. When using this approach, a "shrink-wrap" type of container may be used in which the container conforms to the shape of the allograft as the air is vacuumed out.

Although not required by the present invention, the bone allograft may optionally be freeze-dried prior to insertion in the container where it is then re-hydrated and kept hydrated. An advantage of such optional freeze-drying is that it may reduce the antigenicity of the bone allograft.

Advantages of the bone allograft storage packaging system of the present invention include the elimination of refrigeration requirements, thereby providing allografts that can be quickly prepared for use by a physician when performing a medical procedure. This reduces the overall cost of system operation, since refrigeration equipment is no longer required when storing or transporting the allograft material. A second advantage is that a considerable amount of time is saved by not having to thaw or re-hydrate the allograft material before transplanting it into a patient.

Preferably, the packaging material and the saline solution may be sterilized such that the bone allograft can be removed ready for use in a sterilized condition.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The bone allograft packaging system and related methods disclosed herein boasts a variety of inventive features and components that warrant patent protection, both individually and in combination.

Figure 1:
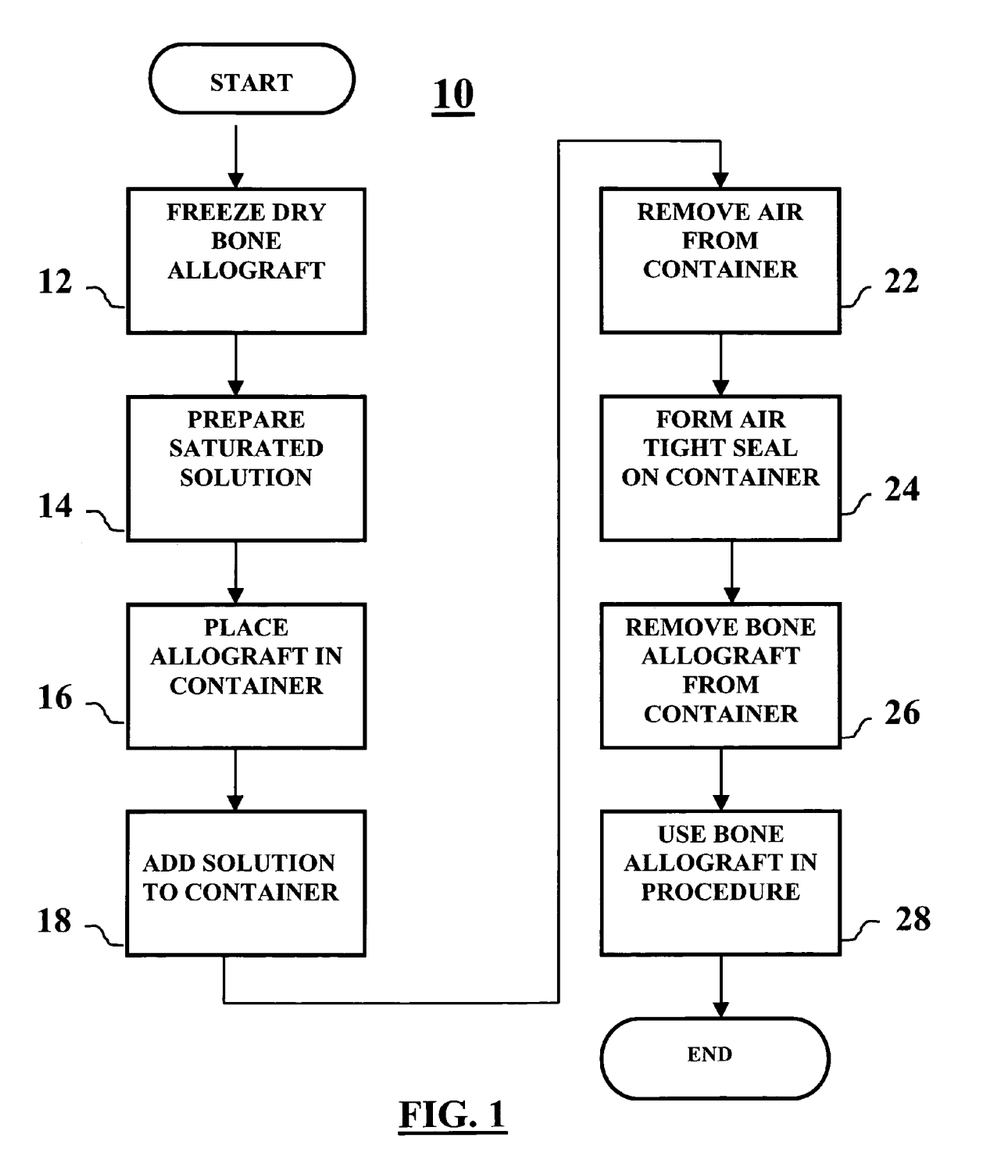
FIG. 1 is a flowchart of a method of packaging a bone allograft for storage to be used in a future medical procedure in accordance with the present invention.

FIG. 1 is a flowchart of one method 10 of packaging and storing a bone allograft for use in a future medical procedure. In accordance with the present invention, the bone allograft is placed in an airtight container in a saturated saline solution, such that the bone allograft may be removed for use just prior to the medical procedure. In one optional aspect, method 10 includes freeze-drying the bone allograft (step 12). Advantageously, freeze-drying the bone allograft may reduce antigenicity of the bone allograft. In other preferred aspects of the present invention, however, this freeze-drying step (12) is bypassed. A saturated solution is prepared (step 14) to be added into the container (step 18). The addition of saline solution to the container may be carried out after, before or concurrently with the placement of the bone allograft in the container (step 16). A simple (i.e.: non-saturated) saline solution may also be used so that step 14 (the preparation of a saturated saline solution) may also be bypassed in some aspects of the invention.

Figure 2:
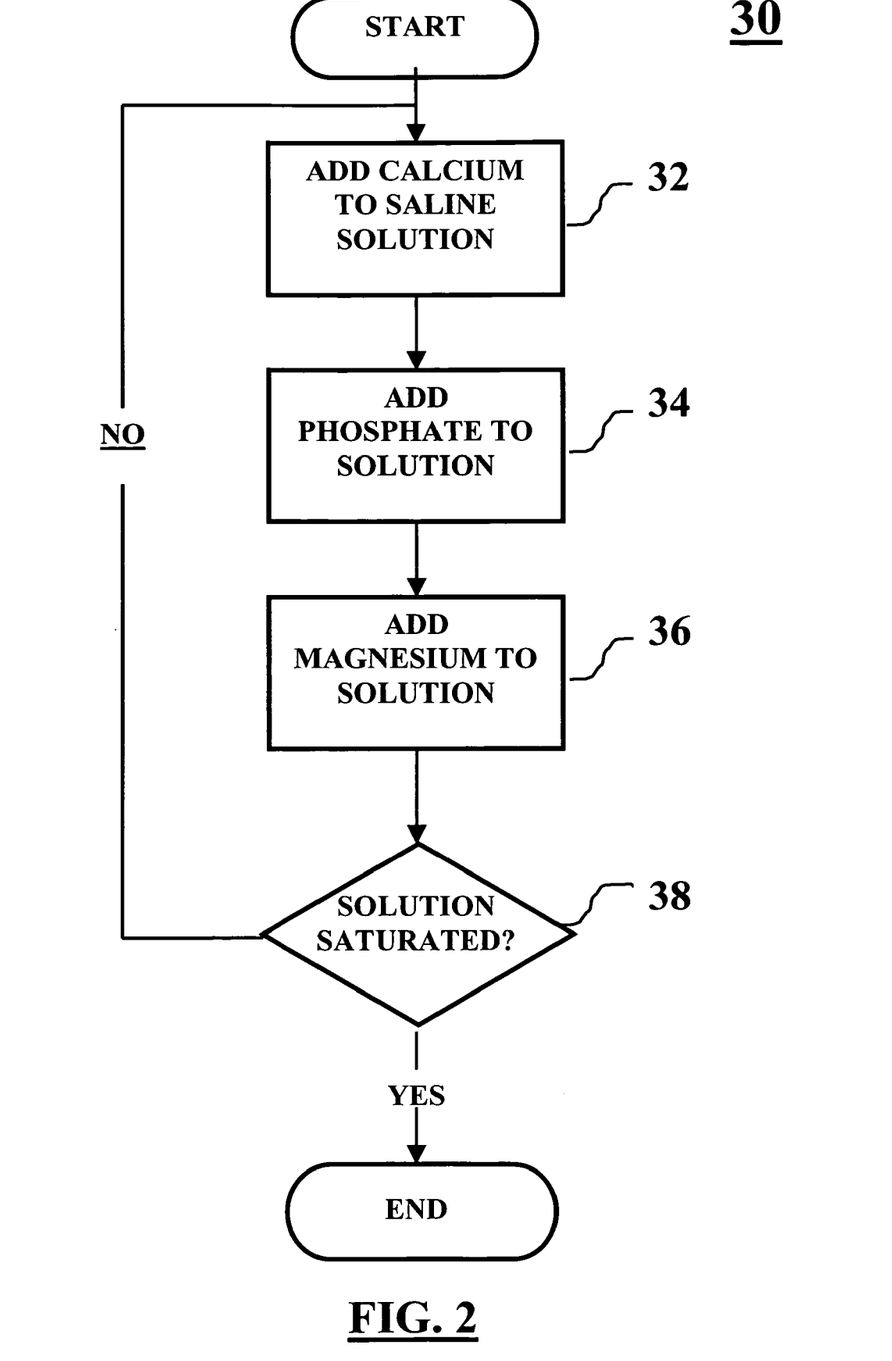
FIG. 2 is a flowchart of a method of preparing a saturated saline solution for use in the method shown in FIG. 1.

One exemplary method 30 of preparing the saturated solution (step 14) is shown in FIG. 2. (The present invention is not limited to this particular method of preparing a saline solution. Rather, any suitable method of preparing the saline solution is also within the scope of the present invention).

As shown in FIG. 2, calcium may optionally be added to the solution (step 32), phosphate may optionally be added to the solution (step 34), and magnesium may optionally be added to the solution (step 36) until the solution is saturated (step 38). In accordance with the present invention, none, some or all of steps 32, 34, 36 may be carried out when preparing the saline solution. In addition, the saline solution may optionally be buffered (to have a neutral pH). The solution so prepared (which may comprise a calcium, phosphate, magnesium salt saturated saline solution) is then added to the bone allograft in the container (step 18). In various optional aspects, other minerals or elements may also be added to the solution, advantageously decreasing mineral leaching from the bone allograft during storage in the container.

Optionally, the amount of solution added to the container is just sufficient to keep the bone allograft hydrated. The solution may optionally be a saline solution or a saturated saline solution. In various optional aspects of the invention in which the bone allograft is freeze dried (step 12) prior to being placed in the container, the amount of solution added is preferably just sufficient to re-hydrate the bone allograft and keep the bone allograft hydrated.

In various aspects of the present invention, the container 40 (FIG. 3) in which allograft 42 is stored may be made from glass, plastic, metal foil, or a combination of these or different materials. Container 40 may optionally be sealed with an airtight seal (step 24 in FIG. 1), for example by a lid 44 placed over container 40 (preferably after air is evacuated (step 22) from container 40). After the air has been evacuated from container 40, bone allograft 42 may then be packaged and stored in a saturated solution 46 (prepared as described above) in container 40, which is preferably airtight. Immediately before allograft 42 is required for use, lid 44 is removed from container 40 and allograft material 42 is removed, already being in a hydrated state.

Figure 3:
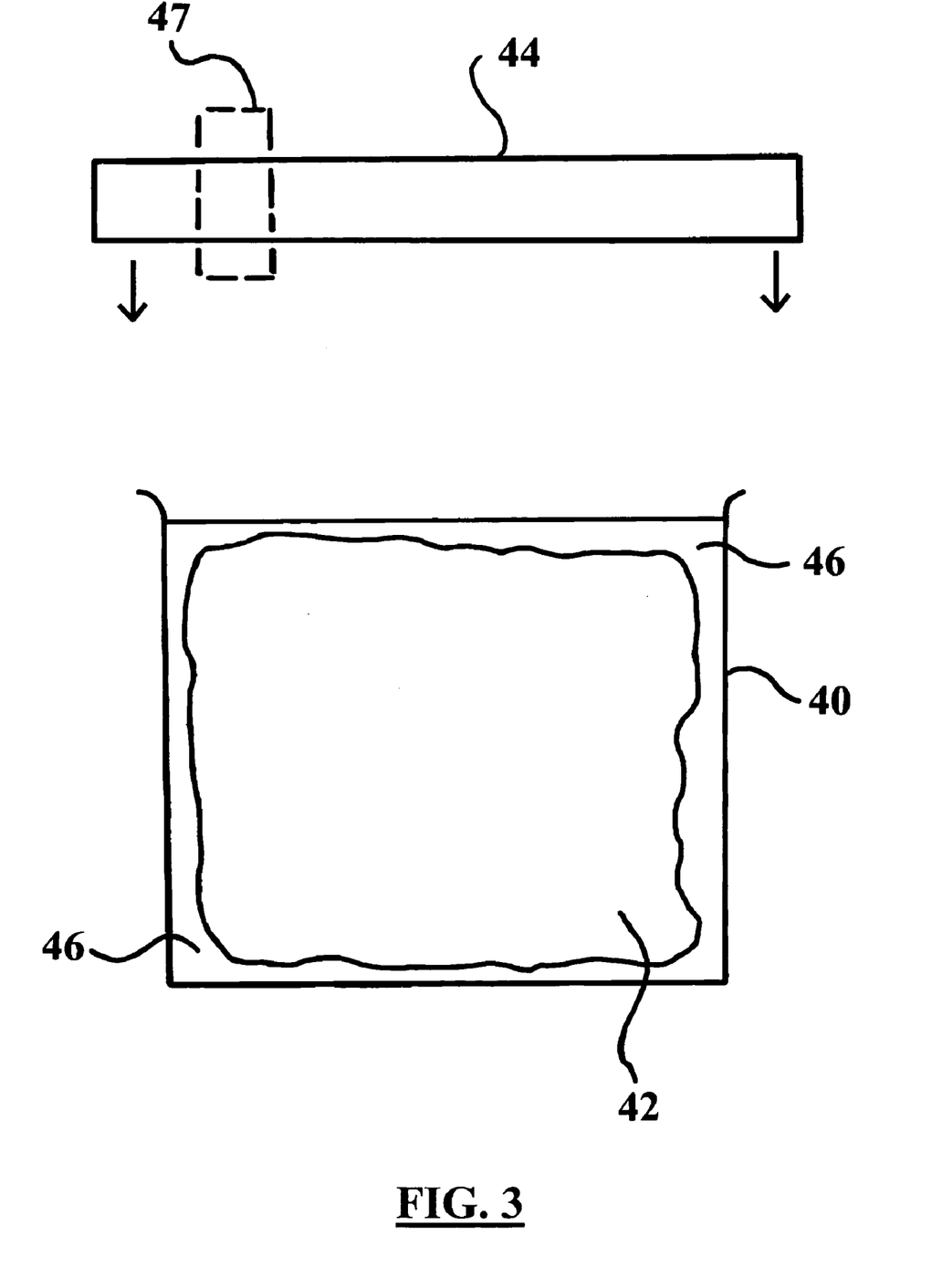
FIG. 3 is an illustration of bone allograft material stored in a saline solution in a container in accordance with the present invention.
Figure 5A:
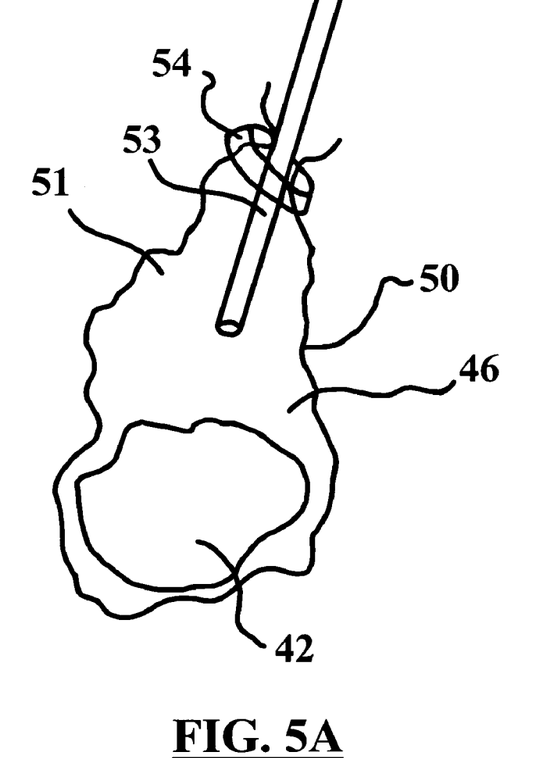
FIGS. 5A and 5B are illustrations of bone allograft material stored in a saline solution in a shape conformable "shrink-wrap" type container in accordance with another method of the present invention.
Figure 5B:
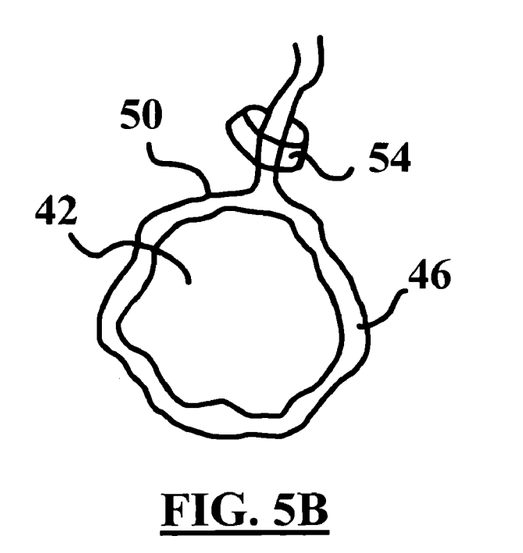

For illustration purposes, allograft 42 is shown submersion in solution 46 in FIGS. 3 & 5. It is to be understood that although allograft 42 is submersed in solution 46 in some cases, the present system requires only enough of solution 46 be used to keep allograft 42 hydrated.

Advantageously, due to the saturation of the solution, the amount of materials leaching from bone allograft 42 into solution 46 will be minimal. In addition, the presence of calcium, phosphate, and magnesium salts in solution 46 may encourage re-mineralization of the bone allograft during storage in container 40. Consequently, bone allograft 42 may conceivably be stored for an indefinite period of time prior to use in a medical procedure.

A further advantage of the present packaging/storage system is that the bone allograft need not be kept in a low temperature environment either during storage in the packaging or during transportation to a medical facility. As such, the bone allograft may advantageously be kept at room temperature during both storage and transportation. As explained above, prior to use in a medical procedure, the bone allograft is simply removed (step 26 in FIG. 1) from the sealed container for use in the medical procedure (step 28 in FIG. 1).

Figure 4A:
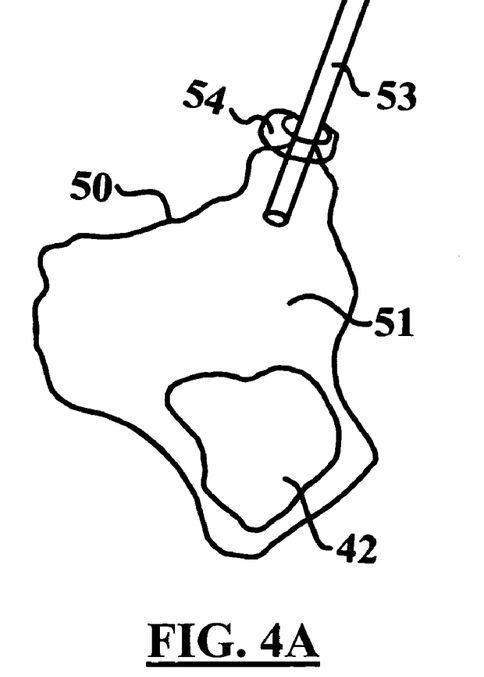
FIGS. 4A and 4B are illustrations of bone allograft material stored in a saline solution in a shape conformable "shrink-wrap" type container in accordance with the present invention.
Figure 4B:
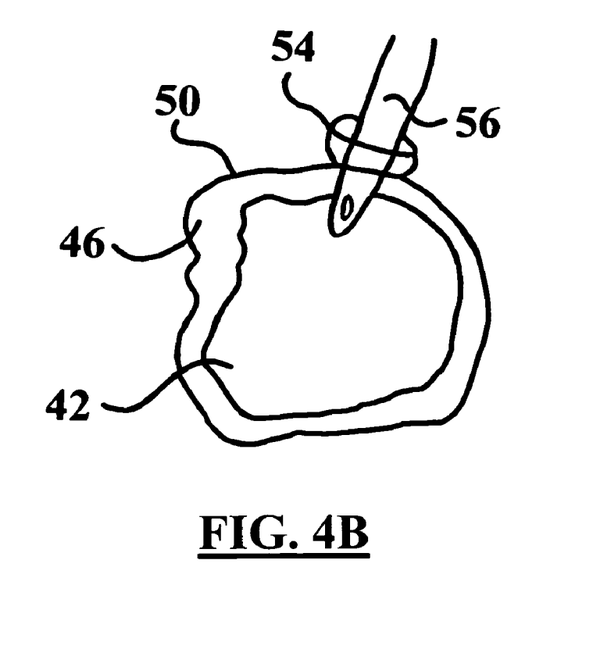

In another optional preferred aspect of the invention shown in FIGS. 4A & 4B, bone allograft 42 is sealed and packaged in a "shrink-wrap" type of shape-conforming material 50. Conforming material 50 may include foil and plastic. In one approach, bone allograft 42 is placed into conforming material 50, air 51 is removed by tube 53, causing conforming material 50 to become "shrink wrapped" around bone allograft 42 as shown in FIG. 4B. Thereafter, solution 46 is added into the shrink wrapped package of conforming material 50, for example by needle 56 inserted through self-sealing valve 54, thereby keeping allograft material 42 hydrated and readied for immediate or near-immediate use. In this aspect of the invention, the amount of solution added to the packaging is preferably just sufficient to keep the bone allograft hydrated.

Alternatively, as shown in FIGS. 5A & 5B, bone allograft 42 and solution 46 can be first added together into conforming material 50, which is then shrink fitted over hydrated allograft 42 by removing air 51 and a portion of solution 46. Specifically, as shown in FIG. 5A, bone allograft 42 is placed into conforming material 50. Thereafter, air 51 is vacuum removed from conforming material 50 such that it wraps tightly around bone allograft 42 as shown in FIG. 5B.

In this aspect of the invention, a portion of solution 46 may also be removed from conforming material 50 as air 51 is removed. However, sufficient solution 46 remains within conforming material 50 (and specifically within bone allograft 42) such that bone allograft 42 remains hydrated, and ready for immediate or near-immediate use. As shown in FIG. 5A, a suction tube 53 may be used to remove air 51 (and a portion of solution 46). As shown in FIG. 5B, a clamp (or a self-sealing valve) 54 may be used to prevent air from entering the package provided by conforming material 50.

In another optional aspect of the invention, solution 46 may be inserted in container 40 (FIG. 3) by first inserting a hollow needle (not shown) through an optional self sealing valve 47 passing through lid 44 and then injecting the solution through the needle.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method of avoiding the need to refrigerate bone allograft during at least one of storage and transportation of the allograft material prior to performing spinal fusion surgery, comprising:
   providing within a sealed container a bone allograft dimensioned for use in a spinal fusion procedure; and
   providing a volume of saline solution within said sealed container.

2. The method of avoiding the need to refrigerate bone allograft during at least one of storage and transportation of the allograft material prior to performing spinal fusion surgery of claim 1, wherein said sealed container comprises:
   a volume surrounded by a material with at least one opening in at least a portion of said material; and
   a mechanism for sealing said container.

3. The method of avoiding the need to refrigerate bone allograft during at least one of storage and transportation of the allograft material prior to performing spinal fusion surgery of claim 2, wherein said material consists primarily of at least one of plastic, glass, and metal foil.

4. The method of avoiding the need to refrigerate bone allograft during at least one of storage and transportation of the allograft material prior to performing spinal fusion surgery of claim 2, wherein said mechanism for sealing said container comprises a lid dimensioned to provide an airtight seal over said at least one opening in at least a portion of said material.

5. The method of avoiding the need to refrigerate bone allograft during at least one of storage and transportation of the allograft material prior to performing spinal fusion surgery of claim 2, wherein said mechanism for sealing said container comprises a self-sealing valve dimensioned to provide an airtight seal over said at least one opening in at least a portion of said material.

6. The method of avoiding the need to refrigerate bone allograft during at least one of storage and transportation of the allograft material prior to performing spinal fusion surgery of claim 5, wherein said saline solution is added to said container via said self-sealing valve after said container is sealed.

7. The method of avoiding the need to refrigerate bone allograft during at least one of storage and transportation of the allograft material prior to performing spinal fusion surgery of claim 1, wherein said container is self-conforming to the shape of said bone allograft.

8. The method of avoiding the need to refrigerate bone allograft during at least one of storage and transportation of the allograft material prior to performing spinal fusion surgery of claim 1, wherein said saline solution is a saturated saline solution.

9. The method of avoiding the need to refrigerate bone allograft during at least one of storage and transportation of the allograft material prior to performing spinal fusion surgery of claim 8, wherein said saturated saline solution comprises saline solution to which at least one of calcium, phosphate, and magnesium has been added until the solution is saturated.

10. The method of avoiding the need to refrigerate bone allograft during at least one of storage and transportation of the allograft material prior to performing spinal fusion surgery of claim 1, wherein said saline solution is provided in a volume just sufficient to hydrate said bone allograft.

11. The method of avoiding the need to refrigerate bone allograft during at least one of storage and transportation of the allograft material prior to performing spinal fusion surgery of claim 1, wherein said saline solution is provided in a volume sufficient to maintain said bone allograft in a substantially submerged state such that said bone allograft will be maintained in a hydrated state until use.

12. The method of avoiding the need to refrigerate bone allograft during at least one of storage and transportation of the allograft material prior to performing spinal fusion surgery of claim 1, wherein providing said bone allograft within said sealed container comprises:
   freeze-drying said bone allograft prior to introduction into said container;
   placing said bone allograft in said container; and
   sealing said container.

13. The method of avoiding the need to refrigerate bone allograft during at least one of storage and transportation of the allograft material prior to performing spinal fusion surgery of claim 12, wherein placing said bone allograft in said container comprises adding a saline solution to said container until said bone allograft is re-hydrated.

14. A method of providing a bone allograft for use in spinal fusion surgery, comprising:
   providing an article of human bone processed to form a bone allograft dimensioned for use in spinal fusion surgery; and
   sealing said bone allograft in a container having a volume of saline solution disposed therein to maintain said bone allograft in a hydrated state prior to use in spinal fusion surgery.

15. The method of providing a bone allograft for use in spinal fusion surgery of claim 14, wherein sealing said bone allograft within said container comprises:
   freeze-drying said bone allograft prior to introduction into said container;
   placing said bone allograft in said container; and
   sealing said container.

16. The method of providing a bone allograft for use in spinal fusion surgery of claim 14, wherein placing said bone allograft in said container comprises adding said saline solution to said container until said bone allograft is re-hydrated.

17. The method of providing a bone allograft for use in spinal fusion surgery of claim 14, wherein said container comprises:
   a volume surrounded by a material with at least one opening in at least a portion of said material; and
   a mechanism for sealing said container.

18. The method of providing a bone allograft for use in spinal fusion surgery of claim 17, wherein said material consists primarily of at least one of glass, plastic, and metal foil.

19. The method of providing a bone allograft for use in spinal fusion surgery of claim 17, wherein said mechanism for sealing said container comprises a lid dimensioned to provide an airtight seal over said at least one opening in at least a portion of said material.

20. The method of providing a bone allograft for use in spinal fusion surgery of claim 17, wherein said mechanism for sealing said container comprises a self-sealing valve dimensioned to provide an airtight seal over said at least one opening in at least a portion of said material.

21. The method of providing a bone allograft for use in spinal fusion surgery of claim 20, wherein said saline solution is added to said container via said self-sealing valve after said container is sealed.

22. The method of providing a bone allograft for use in spinal fusion surgery of claim 14, wherein said container is self-conforming to the shape of said bone allograft.

23. The method of providing a bone allograft for use in spinal fusion surgery of claim 14, wherein said saline solution is a saturated saline solution.

24. The method of providing a bone allograft for use in spinal fusion surgery of claim 23, wherein said saturated saline solution comprises saline solution to which at least one of calcium, phosphate, and magnesium has been added until the solution is saturated.

25. The method of providing a bone allograft for use in spinal fusion surgery of claim 14, wherein said saline solution is provided in a volume just sufficient to hydrate said bone allograft.

26. The method of providing a bone allograft for use in spinal fusion surgery of claim 14, wherein said saline solution is provided in a volume sufficient to maintain said bone allograft in a substantially submerged state such that said bone allograft will be maintained in a hydrated state until use.

* * * * *